(12) United States Patent
Zhang et al.

(10) Patent No.: US 10,407,700 B2
(45) Date of Patent: Sep. 10, 2019

(54) SURFACTANT-IMPROVED SIMULTANEOUS SACCHARIFICATION AND CO-FERMENTATION METHOD FOR LIGNOCELLULOSE

(71) Applicant: DALIAN INSTITUTE OF CHEMICAL PHYSICS, CHINESE ACADEMY OF SCIENCES, Dalian (CN)

(72) Inventors: Zongchao Zhang, Dalian (CN); Xiumei Liu, Dalian (CN); Liaoyuan Mao, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 198 days.

(21) Appl. No.: 15/521,920

(22) PCT Filed: Dec. 29, 2014

(86) PCT No.: PCT/CN2014/001188
§ 371 (c)(1),
(2) Date: Apr. 26, 2017

(87) PCT Pub. No.: WO2016/077942
PCT Pub. Date: May 26, 2016

(65) Prior Publication Data
US 2017/0321231 A1 Nov. 9, 2017

(30) Foreign Application Priority Data
Nov. 20, 2014 (CN) .......................... 2014 1 0668100

(51) Int. Cl.
*C12P 7/14* (2006.01)
*C12P 7/10* (2006.01)
*C10L 1/02* (2006.01)

(52) U.S. Cl.
CPC ................ *C12P 7/14* (2013.01); *C10L 1/02* (2013.01); *C12P 7/10* (2013.01);
(Continued)

(58) Field of Classification Search
CPC .... C12P 7/04; C12P 19/02; C12P 7/18; C12P 19/14; C12P 7/10; C12P 7/20; C12P 7/56; C12P 19/20; C12P 7/06; C12P 2201/00; C12P 7/14; C12P 2203/00; C12P 5/023; C12P 19/24; C12P 21/02; C12P 7/46; C12P 13/14; C12P 7/16; C12P 7/48; C12P 7/54; C12P 7/58; C12P 13/001; C12P 7/40; Y02E 50/16; Y02E 50/17; Y02E 50/13; Y02E 50/343; Y10T 442/60; Y10T 428/13; Y10T 428/1352; Y10T 428/139; C07K 14/37; C11B 1/025; C07G 1/00; C12N 9/2414; C12N 9/242; C12N 9/0061; C12N 9/2437; C12N 9/92; C12N 1/38; C12N 9/90; C12N 1/22; C12N 9/001; C12N 9/0059; C12N 9/0071; C12N 9/2445; C12N 15/80; C12N 15/81; C12N 9/0006; C12N 9/2428; C12N 9/2434; C12Y 302/01001; C12Y 302/01004; C12Y 302/01003; C12Y 302/01021; C12Y 503/01005; C12Y 101/01009; C12Y 201/01017; C12Y 302/01091; B09B 3/00; C13K 1/02; C13K 13/002; C13K 13/007; C13K 13/00; C10L 1/02; C10L 2200/0469; C10L 2290/26; C10L 1/003; C10L 1/026; C10L 1/04; C10L 1/06; C10L 1/08; C10L 1/1802; C11D 3/38636; C11D 3/3864; C11D 1/66; C11D 3/382; C11D 3/386; C11D 3/38609; C11D 3/38618; D21C 1/04; D21C 1/02; D21C 5/005; D21C 3/04; D21C 11/0007;
(Continued)

(56) References Cited

U.S. PATENT DOCUMENTS 8,728,770 B2 * 5/2014 Ishikawa ................. C12P 19/02
435/100
9,512,495 B2 * 12/2016 Eyal ......................... C08H 8/00
(Continued)

FOREIGN PATENT DOCUMENTS

CN        102226204 B        4/2013

OTHER PUBLICATIONS

International Search Report dated Feb. 6, 2015 for related PCT Application No. PCT/CN2014/001188 by State Intellectual Property Office of the P.R. China.
(Continued)

*Primary Examiner* — Deborah K Ware
(74) *Attorney, Agent, or Firm* — Enshan Hong; VLP Law Group LLP (57) ABSTRACT

A surfactant-improved simultaneous saccharification and co-fermentation method for lignocelluloses in which a pretreated lignocellulose substrate is directly subjected to surfactant-improved simultaneous saccharification and co-fermentation without any detoxification by adding a surfactant, and the surfactant may be selectively added before or after pre-enzymatic hydrolysis, having economic, effective and feasible application prospects in reducing the loss of glucose, simplifying the production process, reducing equipment investment, reducing water consumption, improving ethanol production and reducing the total cost of the ethanol production process.

8 Claims, 3 Drawing Sheets

(52) U.S. Cl.
CPC .............. *C12Y 302/01004* (2013.01); *C10L 2200/0469* (2013.01); *C10L 2290/26* (2013.01); *C12P 2201/00* (2013.01); *Y02E 50/16* (2013.01)

(58) Field of Classification Search
CPC .......... D21C 3/00; D21C 5/022; D21C 11/00; Y02P 20/125; A23K 20/163; A23K 50/10; C07H 1/00; C07H 3/00; C08H 6/00; C08H 8/00; A61L 15/20; A61L 15/42; C07C 57/04; C08K 3/20; C08L 97/02

See application file for complete search history.

(56) References Cited

U.S. PATENT DOCUMENTS

| | | | | |
|---|---|---|---|---|
| 9,816,082 | B2* | 11/2017 | Sweeney | C12Y 302/01004 |
| 10,066,243 | B2* | 9/2018 | Zhang | C12P 7/06 |
| 10,087,476 | B2* | 10/2018 | Foody | C07G 1/00 |
| 2008/0227166 | A1* | 9/2008 | Allain | 435/161 |
| 2009/0311752 | A1* | 12/2009 | Bodie | C12N 1/22 |
| | | | | 435/72 |
| 2011/0008863 | A1* | 1/2011 | Zhu | C12P 7/10 |
| | | | | 435/165 |
| 2011/0171685 | A1* | 7/2011 | Li | C12P 19/02 |
| | | | | 435/41 |
| 2012/0028299 | A1* | 2/2012 | Li | C12N 1/22 |
| | | | | 435/41 |
| 2013/0052702 | A1* | 2/2013 | Saunders | C07K 14/37 |
| | | | | 435/134 |
| 2016/0010127 | A1* | 1/2016 | Wu | C12P 19/14 |
| | | | | 435/139 |

OTHER PUBLICATIONS

Zhang et al., Food and Fermentation Industries., 38, 50-54 (2012) (English abstract is provided).
Wang et al., Bioresource Technology, 101, 7995-8000 (2010).
Written Opinion of the International Search Authority dated Feb. 6, 2015 for related PCT Application No. PCT/CN2014/001188 by State Intellectual Property Office of the P.R. China.
Kim et al., Bioprocess Biosyst. Eng. (2013) 36:659-666.
Yu et al., Bioresource Technology, 2011, 102(8): 5123-5128.

* cited by examiner

Fig.6

SURFACTANT-IMPROVED SIMULTANEOUS SACCHARIFICATION AND CO-FERMENTATION METHOD FOR LIGNOCELLULOSE

PRIORITY CLAIM

This is a U.S. national stage of application No. PCT/CN2014/001188 filed on Dec. 29, 2014, which claims priority from China Patent Application Nos. 201410668100.1 filed Nov. 20, 2014, the entire content of which is incorporated herein as reference.

BACKGROUND OF THE INVENTION

1. Field of the Invention

The present invention relates to the field of the production of fuel ethanol by the fermentation process of biomass feedstock degradation, and more particularly to a surfactant-improved simultaneous saccharification and co-fermentation method for lignocellulose.

2. Description of Related Arts

With the increasing depletion of fossil fuels and the increasing pollution of the environment, the development and utilization of renewable clean energy fuels has received widespread attention. Traditional ethanol fermentation of sugar or starch as raw material, both of which are the main source of food, food as raw material to produce fuel ethanol has posed a threat to world food security, looking for other raw materials to replace food is imperative. Lignocellulose is the most abundant and inexpensive renewable resource in nature. Its main component cellulose hemicellulose is a potential raw material for the production of fuel ethanol. The production of fuel ethanol from lignocellulose has become a hot topic in the world. The production of fuel ethanol from lignocellulose is subject to three steps: pretreatment, enzymolysis and fermentation. However, toxic substances such as weak acid, furfural and 5-hydroxymethylfurfural (HMF) and phenolic compounds are produced during the biomass pretreatment: these compounds have a strong inhibitory effect on the fermentation of Saccharomyces cerevisiae, which affects the normal growth of yeast and the subsequent fermentation process.

Therefore, it is particularly important to detoxify the pretreated lignocellulosic hydrolyzate. The detoxification methods reported in the literature mainly include water detoxification, physical detoxification (vacuum concentration gas extraction method, membrane separation method), chemical detoxification (lime neutralization, activated carbon adsorption, ion exchange, solvent extraction), biological detoxification, for example, Bioprocess Biosyst Eng (2013) 36: 659-666 discusses the effects of fermentation inhibitors such as furfural, HMF and levulinic acid on the growth rate of yeast cells by activated carbon adsorption. Patent No. CA102226204B discloses a lignocellulosic ethanol fermentation broth by adding a soluble electrolyte salt to the sugar solution to be treated and heating to obtain a constant temperature raw material liquid by membrane distillation to remove the saccharide from the subsequent fermentation to inhibit the role of substances. However, washing, physical, chemical detoxification, etc., consume a lot of water resources, equipment investment costs are high and the process is complex, and the detoxification effect is poor, sugar loss is serious; Yanling Yu reported a biological detoxification method (Bioresource Technology, 2011, (8): 5123-5128). The germination of corn stalk steam explosion was carried out by using Aspergillus nidulans (FLZ10), and then the fermentation was carried out by using Saccharomyces cerevisiae. The ethanol concentration reached 34 g/L. The method requires the addition of Aspergillus nidulans for equipment investment, culture medium and energy consumption. Therefore, the improvement of a simple, low cost, good detoxification process is the only way which must be passed for the wood fiber-ethanol industry.

SUMMARY OF THE INVENTION

The object of the present invention is to provide a surfactant-improved simultaneous saccharification and co-fermentation method for lignocellulose in which the lignocellulose is used as a raw material, which is directed to the inhibitory effect of the toxic substances produced in the conventional biomass pretreatment process on the subsequent fermentation process.

In order to achieve the object of the present invention, a surfactant-improved simultaneous saccharification and co-fermentation method (SSCF) for lignocellulose is provided by the present invention to directly treat the pretreated cellulose substrate without any detoxification treatment by continuously enzymatic hydrolysis; the surfactant may be optionally added before or after pre-enzymolysis.

The specific steps of adding the surfactant to the pre-enzymatic solution are as follows: using the pretreated lignocellulose s a substrate, and adding firstly the cellulase, the water-soluble surfactant and the pH buffer under the high temperature condition for a period of time, and then lowering the temperature and adding Saccharomyces cerevisiae for simultaneous saccharification and ethanol fermentation production.

When the surfactant is selectively added after pre-enzymatic hydrolysis, the specific steps are as follows: using the pre-treated lignocellulose as a substrate, and adding firstly the cellulase, a pH buffer under high temperature conditions for a period of time, and then lowering the temperature and adding the surfactant and Saccharomyces cerevisiae for simultaneous saccharification and ethanol fermentation.

In the fermentation system, the solid-liquid ratio of the pretreated lignocellulose and the buffer is 0.1-0.3 g/mL; the concentration of the water-soluble surfactant is 0-0.4 g/mL; the loading of the cellulase added is 10-30 FPU/g dry lignocellulose, and the cell density of the Saccharomyces cerevisiae is $0.5*10^8$-$1.8*10^8$ cells/mL; the pre-enzymatic hydrolysis temperature is 50° C., the pre-enzymolysis time is 2-24 hours; and ethanol fermentation production temperature is 30-39° C.; simultaneous saccharification and ethanol fermentation time is 16-96 hours, 150-300 rpm.

The surfactant includes at least one of polyethylene glycol (PEG), polyethylene glycol monomethyl ether (MPEG), polyethylene glycol dimethyl ether (NHD), polydimethylsiloxane (PMDS), or combinations thereof in any proportion.

The water-soluble surfactant is preferably polyethylene glycol (PEG) having a molecular weight of from 200 to 8000, and more preferably from 200 to 2,000.

The pH buffer solution of the table is: acetic acid-sodium acetate, citric acid-sodium citrate, phosphoric acid-sodium phosphate buffer, or sulfuric acid solution, the pH buffer solution has a pH value of 4.0-5.5.

The pH value of the pH buffer solution is preferably 4.8.

The concentration of the water-soluble surfactant is preferably 0.125-0.18 g/mL.

The solid-liquid ratio of the pretreated lignocellulose and the buffer in the fermentation system is preferably 0.125 g/mL.

The loading of the cellulase added in the fermentation system is preferably 20 FPU/g dry lignocellulose.

The cell density of *Saccharomyces cerevisiae* in the fermentation system is preferably $0.6*10^8$-$0.96*10^8$ cells/mL.

The pre-enzymatic hydrolysis time is preferably 8-12 hours; the temperature of the simultaneous saccharification and ethanol fermentation is preferably 33° C., and the simultaneous saccharification and ethanol fermentation time is preferably 72 hours.

Figure 1:
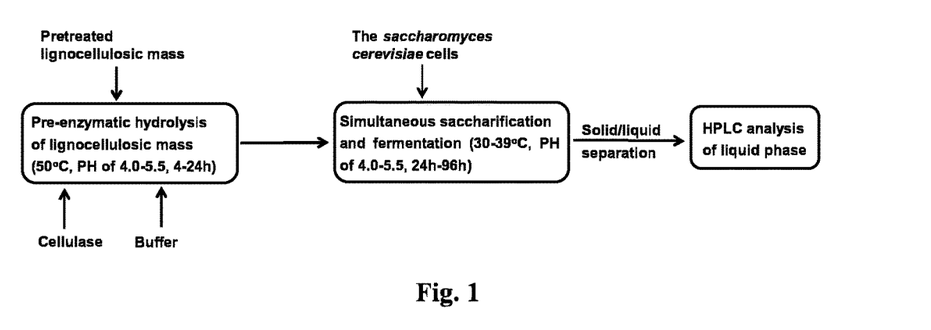
FIG. 1 illustrates an operation of SSCF in pure water.
Figure 2:
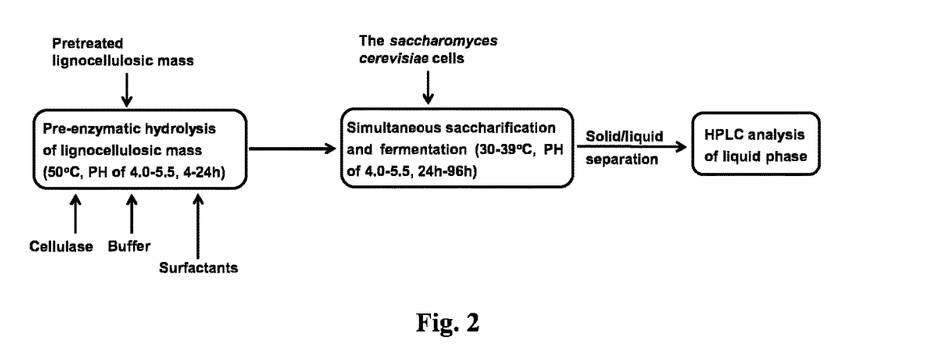
FIG. 2 illustrates an operation 1 of a surfactant-improved SSCF.
Figure 3:
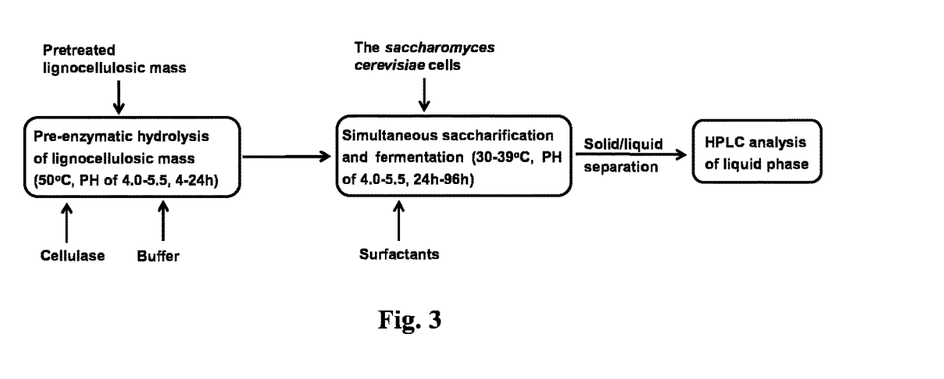
FIG. 3 illustrates an operation 2 of a surfactant-improved SSCF.

The specific SSCF process can be seen in FIG. 1, FIG. 2 and FIG. 3.

The prior art utilizes pretreated lignocellulose as raw material, firstly add cellulase, a pH buffer under high temperature conditions for pre-enzymatic hydrolysis for a period of time, and then lower the temperature and add *Saccharomyces cerevisiae* for simultaneous saccharification and ethanol fermentation production, shown in FIG. 1. The process of the surfactant-improved lignocellulose simultaneous saccharification and co-fermentation method (SSCF) of the present invention is shown in FIG. 2 and FIG. 3.

Compared with the prior art, the present invention has the following advantages: the pretreated cellulose substrate can be directly fermented by continuous enzymatic saccharification and co-fermentation without detoxification via the addition of the surfactant, and it has economic, effective and feasible application prospects in reducing the loss of glucose, simplifying the production process, reducing equipment investment, reducing water consumption and improving ethanol production and so on. For the first time, the present invention ferments fast-growing poplar without detoxification by adding a surfactant and the simultaneous saccharification and co-fermentation method to produce ethanol, and the concentration and yield of ethanol has been improved and the total cost of the ethanol production process from lignocellulosic to ethanol is effectively reduced.

For example, in the steam explosion process, the concentration of the pretreated fast-growing poplar is 15%, the simultaneous saccharification and co-fermentation time is 96 hours, when without the addition of the surfactant, the concentration of ethanol is 22% and 7.0 g/L, and when adding 1.5 g/mL surfactant, the yield and concentration of ethanol is 75% and 24.0 g/L, respectively.

DETAILED DESCRIPTION OF THE PREFERRED EMBODIMENT

The present invention will be described in further detail with reference to specific embodiments, but the scope of the invention is not to be limited by the scope of the present invention, and the following description of the invention and the description are merely illustrative of the principles of the present invention without departing from the spirit and scope of the present invention It will be understood that various changes and modifications may be made therein without departing from the scope of the present invention as claimed. It is intended that the scope of the present invention be defined by the appended claims and their equivalents.

In addition, it is worth mentioning that the content of each component in the fermentation in each of the following examples is determined by a high performance liquid chromatograph (Agilent 1260), and the conversion rate and ethanol yield are calculated based on the amount of the dropped lignocellulosic substrate, and the ethanol concentration is calculated according to the mass of ethanol in the fermentation broth, the volume of activated water and the pH value thereof.

The conditions of chromatographic are as follows: ion exchange column, column temperature 65° C., parallax refractive index detector, detector temperature 50° C.; mobile phase: 5 Mm $H_2SO_4$, flow rate 0.6 mL/min, injection volume 25 uL.

The pretreatment method described in the examples of the present invention is the steam explosion method.

Example 1

The pretreated fast-growing poplar powder of 1.5 g is used as a substrate, and firstly adding 10.5 mL buffer solution, 0.2 mL cellulase, wherein the buffer solution has a pH value of 4.86, incubating for 4 hours at a temperature of 50° C., and then lowering the temperature to 33° C., then adding *Saccharomyces cerevisiae*, wherein the cell density is maintained $0.8*10^8$/mL, SSCF fermentation for 72 hours. The enzymatic hydrolysis rate, ethanol yield and concentration data of the pretreated fast-growing poplar are shown in Table 1.

Example 2

The pretreated fast-growing poplar powder of 1.5 g is used as a substrate, and firstly adding 10.5 mL buffer solution, 0.2 mL cellulase and 2.0 g PEG-1000, wherein the buffer solution has a pH value of 4.86, incubating for 4 hours at a temperature of 50° C., and then lowering the temperature to 33° C., then adding *Saccharomyces cerevisiae*, wherein the cell density is maintained $0.8*10^8$/mL, SSCF fermentation for 72 hours. The enzymatic hydrolysis rate, ethanol yield and concentration data of the pretreated fast-growing poplar are shown in Table 1. It can be seen from the data in the table that the hydrolysis rate has almost no change after adding PEG-1000, while the ethanol yield and concentration is increased by nearly 1 times.

Example 3

The experimental procedure is the same as in Example 1 except that the yeast cell density is $0.96*10^8$/mL. The enzymatic hydrolysis rate, ethanol yield and concentration data of the pretreated fast-growing poplar are shown in Table 1. It can be seen from the data in the table that the enzymatic efficiency, ethanol concentration and yield have almost no change after increasing the concentration of yeast cells in pure water system.

Example 4

The experimental procedure is the same as in Example 2 except that the yeast cell density is $0.96*10^8$/mL. The enzymatic hydrolysis rate, ethanol yield and concentration data of the pretreated fast-growing poplar are shown in Table 1. It can be seen from the data in the table that in PEG-1000 system, when the concentration of yeast cells is increased, the enzymatic efficiency, ethanol concentration and yield have almost no change.

Example 5

The experimental procedure is the same as in Example 1 except that the buffer solution is increased to 12.0 mL. The enzymatic hydrolysis rate, ethanol yield and concentration data of the pretreated fast-growing poplar are shown in Table 1. It can be seen from the data in the table that in pure water system, when the concentration of substrate is reduced, the enzymatic efficiency, ethanol concentration and yield have almost no change.

Example 6

The experimental procedure is the same as in Example 2 except that the buffer solution is increased to 12.0 mL. The enzymatic hydrolysis rate, ethanol yield and concentration data of the pretreated fast-growing poplar are shown in Table 1. It can be seen from the data in the table that in PEG-1000 system, when the concentration of substrate is reduced, the enzymatic efficiency, ethanol concentration and yield are significantly improved.

Example 7

The experimental procedure is the same as in Example 1 except that the buffer solution is reduced to 10.0 mL. The enzymatic hydrolysis rate, ethanol yield and concentration data of the pretreated fast-growing poplar are shown in Table 1. It can be seen from the data in the table that in pure water system, when the concentration of substrate is increased, the enzymatic efficiency, ethanol concentration and yield have almost no change.

Example 8

The experimental procedure is the same as in Example 2 except that the buffer solution is reduced to 12.0 mL. The enzymatic hydrolysis rate, ethanol yield and concentration data of the pretreated fast-growing poplar are shown in Table 1. It can be seen from the data in the table that in PEG-1000 system, when the concentration of substrate is decreased, the enzymatic efficiency was decreased, ethanol concentration and yield are significantly increased.

TABLE 1

Simultaneous saccharification and co-fermentation of pretreated fast-growing poplar

| Example | Saccharomyces cerevisiae cells/mL | PEG-1000 | Buffer/mL | Enzymatic hydrolysis rate/% | Ethanol yield/% | Ethanol/g/L |
| --- | --- | --- | --- | --- | --- | --- |
| 1 | $0.8 \times 10^8$ | 0.0000 | 10.5 | 62.2 | 20.3 | 7.57 |
| 2 | $0.8 \times 10^8$ | 2.0901 | 10.5 | 62.7 | 46.5 | 17.30 |
| 3 | $0.96*10^8$ | 0.0000 | 10.5 | 62.8 | 24.3 | 9.05 |
| 4 | $0.96*10^8$ | 2.0072 | 10.5 | 58.1 | 46.9 | 17.46 |
| 5 | $0.8*10^8$ | 0.0000 | 12.0 | 67.1 | 23.0 | 7.52 |
| 6 | $0.8*10^8$ | 2.0209 | 12.0 | 65.5 | 64.3 | 20.94 |
| 7 | $0.96*10^8$ | 0.0000 | 10.0 | 64.5 | 21.9 | 8.55 |
| 8 | $0.96*10^8$ | 2.0342 | 10.0 | 58.3 | 36.9 | 14.44 |

Example 9

The experimental procedure is the same as in Example 5 except that the cellulase is 0.3 mL. The enzymatic hydrolysis rate, ethanol yield and concentration data of the pretreated fast-growing poplar are shown in Table 2. It can be seen from the data in the table that in pure water system, when the concentration of cellulase is improved, the enzymatic efficiency is increased a little, and ethanol concentration and yield have almost no change.

Example 10

The experimental procedure is the same as in Example 6 except that the cellulase is 0.3 mL. The enzymatic hydrolysis rate, ethanol yield and concentration data of the pretreated fast-growing poplar are shown in Table 2. It can be seen from the data in the table that in PEG-1000 system, when the concentration of cellulase is improved, the enzymatic efficiency, ethanol concentration and yield are improved.

Example 11

The experimental procedure is the same as in Example 9 except that the pretreated fast-growing poplar is subjected to pre-enzymatic hydrolysis at 50° C. for 8 hours. The enzymatic hydrolysis rate, ethanol yield and concentration data of the pretreated fast-growing poplar are shown in Table 2. It can be seen from the data in the table that in pure water system, when the co-fermentation time is prolonged in pure water system, the enzymatic efficiency is increased, and ethanol concentration and yield have almost no change.

Example 12

The experimental procedure is the same as in Example 10 except that the pretreated fast-growing poplar is subjected to pre-enzymatic hydrolysis at 50° C. for 8 hours. The enzymatic hydrolysis rate, ethanol yield and concentration data of the pretreated fast-growing poplar are shown in Table 2. It can be seen from the data in the table that in pure water system, when the co-fermentation time is prolonged in the PEG-1000 system, the enzymatic efficiency, ethanol concentration and yield are improved.

Example 13

The experimental procedure is the same as in Example 12 except that PEG-1000 is added after the pretreated fast-growing poplar is subjected to pre-enzymatic hydrolysis. The enzymatic hydrolysis rate, ethanol yield and concentration data of the pretreated fast-growing poplar are shown in Table 2. It can be seen from the data in the table that the order of addition of the surfactant has no significant effect on the fermentation efficiency.

Example 14

The experimental procedure is the same as in Example 10 except that PEG-1000 is 3.0 g. The enzymatic hydrolysis rate, ethanol yield and concentration data of the pretreated fast-growing poplar are shown in Table 2. It can be seen from the data in the table that the excess of PEG-1000 can lead to the decrease of SSCF process efficiency, the enzymolysis efficiency, ethanol concentration and yield are reduced.

TABLE 2

Simultaneous saccharification and co-fermentation of pretreated fast-growing poplar

| Example | PEG-1000 | Time/h | Enzymolysis efficiency/% | Ethanol yield/% | Ethanol/g/L |
|---|---|---|---|---|---|
| 9 | 0.0000 | 4 + 72 | 71.13 | 23.28 | 7.57 |
| 10 | 2.0039 | 4 + 72 | 72.12 | 71.20 | 23.17 |
| 11 | 0.0000 | 8 + 72 | 75.53 | 22.52 | 7.32 |
| 12 | 2.0085 | 8 + 72 | 76.51 | 75.63 | 24.61 |
| 13 | 2.0303 | 8 + 72 | 74.41 | 73.44 | 23.89 |
| 14 | 3.0300 | 4 + 72 | 62.16 | 60.89 | 19.81 |

Example 15

The experimental procedure is the same as in Example 11 except that the pretreated fast-growing poplar is subjected to pre-enzymatic hydrolysis for 24 hours. The enzymatic hydrolysis rate, ethanol yield and concentration data of the pretreated fast-growing poplar are shown in Table 3. It can be seen from the data in the table that in pure water system, the prolonged reaction time of SSCF process does not improve the ethanol concentration and yield.

Example 16

The experimental procedure is the same as in Example 12 except that the pretreated fast-growing poplar is subjected to pre-enzymatic hydrolysis for 24 hours. The enzymatic hydrolysis rate, ethanol yield and concentration data of the pretreated fast-growing poplar are shown in Table 3. It can be seen from the data in the table that in PEG-1000 system, the prolonged reaction time of SSCF process does not improve the ethanol concentration and yield.

Example 17

The experimental procedure is the same as in Example 15 except that the buffer solution is reduced to 10 mL. The enzymatic hydrolysis rate, ethanol yield and concentration data of the pretreated fast-growing poplar are shown in Table 3. It can be seen from the data in the table that in pure water system, when the concentration of substrate is increased in SSCF process, and the ethanol concentration is not improved.

Example 18

The experimental procedure is the same as in Example 12 except that the buffer solution is reduced to 10 mL. The enzymatic hydrolysis rate, ethanol yield and concentration data of the pretreated fast-growing poplar are shown in Table 3. It can be seen from the data in the table that in PEG-1000 system, when the concentration of substrate in SSCF process is increased, the ethanol yield and concentration are significantly reduced, but it is still higher than the pure water system.

TABLE 3

Simultaneous saccharification and co-fermentation of pretreated fast-growing poplar

| Example | PEG-1000 | Buffer/mL | Enzymatic hydrolysis rate/% | Ethanol yield/% | Ethanol/g/L |
|---|---|---|---|---|---|
| 15 | 0.0000 | 12 | 82.88 | 21.55 | 7.01 |
| 16 | 2.0059 | 12 | 76.62 | 75.74 | 24.66 |
| 17 | 0.0000 | 10 | 77.41 | 19.59 | 7.65 |
| 18 | 1.9966 | 10 | 76.12 | 28.42 | 11.10 |

Example 19

The experimental procedure is the same as in Example 16 except that the fermentation temperature is 36° C. The enzymatic hydrolysis rate, ethanol yield and concentration data of the pretreated fast-growing poplar are shown in Table 4. It can be seen from the data in the table that in PEG-1000 system, during the SSCF process, the proper increase of temperature can effectively improve the ethanol yield and concentration.

Example 20

The experimental procedure is the same as in Example 16 except that the fermentation temperature is 39° C. The enzymatic hydrolysis rate, ethanol yield and concentration data of the pretreated fast-growing poplar are shown in Table 4. It can be seen from the data in the table that in PEG-1000 system, during the SSCF process, the proper increase of temperature can effectively improve the ethanol yield and concentration.

Example 21

The experimental procedure is the same as in Example 16 except that the added surfactant is 2.0 g PEG-200. The enzymatic hydrolysis rate and ethanol concentration data are shown in Table 4. It can be seen from the data in the table that PEG-200 can effectively improve the ethanol yield and concentration.

Example 22

The experimental procedure is the same as in Example 16 except that the added surfactant is 2.0 g PEG-400. The enzymatic hydrolysis rate and ethanol concentration data are shown in Table 4. It can be seen from the data in the table that PEG-400 can effectively improve the ethanol yield and concentration.

Example 23

The experimental procedure is the same as in Example 16 except that the added surfactant is 2.0 g PEG-4000. The enzymatic hydrolysis rate and ethanol concentration data are shown in Table 4. It can be seen from the data in the table that PEG-4000 can effectively improve the ethanol yield and concentration.

Example 24

The experimental procedure is the same as in Example 16 except that the added surfactant is 2.0 g polyethylene glycol monomethyl ether (MPEG). The glucose conversion rate and ethanol concentration data are shown in Table 4. It can be seen from the data in the table that MPEG can effectively improve the ethanol yield and concentration.

Example 25

The experimental procedure is the same as in Example 16 except that the added surfactant is 2.0 g polyethylene glycol dimethyl ether (NHD). The glucose conversion rate and ethanol concentration data are shown in Table 4. It can be seen from the data in the table that NHD can effectively improve the ethanol yield and concentration.

TABLE 4

Simultaneous saccharification and co-fermentation of pretreated fast-growing poplar

| Example | Surfactant | Temperature/ °C. | Enzymatic hydrolysis rate/ % | Ethanol yield/% | Ethanol/ g/L |
|---|---|---|---|---|---|
| 19 | PEG-1000 | 55 + 36 | 97.5 | 96.8 | 31.5 |
| 20 | PEG-1000 | 55 + 39 | 89.1 | 89.0 | 29.0 |
| 21 | PEG-200 | 55 + 33 | 77.4 | 60.8 | 19.8 |
| 22 | PEG-400 | 55 + 33 | 76.1 | 66.8 | 22.8 |
| 23 | PEG-4000 | 55 + 33 | 76.6 | 75.7 | 24.6 |
| 24 | MPEG | 55 + 33 | 77.2 | 28.4 | 11.1 |
| 25 | NHD | 55 + 33 | 74.5 | 26.5 | 10.0 |

Example 26

Figure 4:
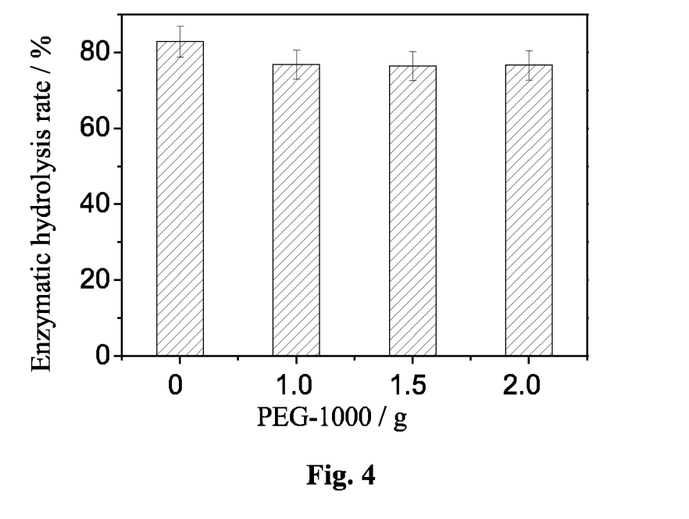
FIG. 4 illustrates effects of different concentrations of PEG-1000 on enzymatic hydrolysis efficiency of non-detoxification steam exploded fast-growing poplar SSCF process.
Figure 5:
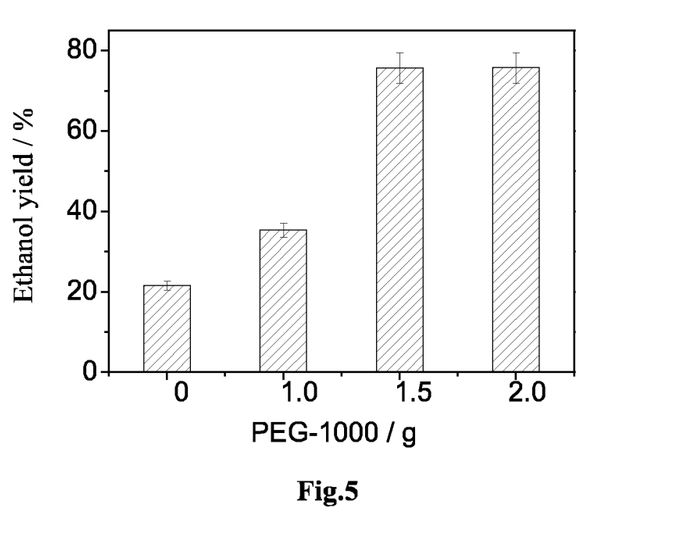
FIG. 5 illustrates effects of different concentrations of PEG-1000 on the ethanol yield of non-detoxification steam exploded fast-growing poplar SSCF process.
Figure 6:
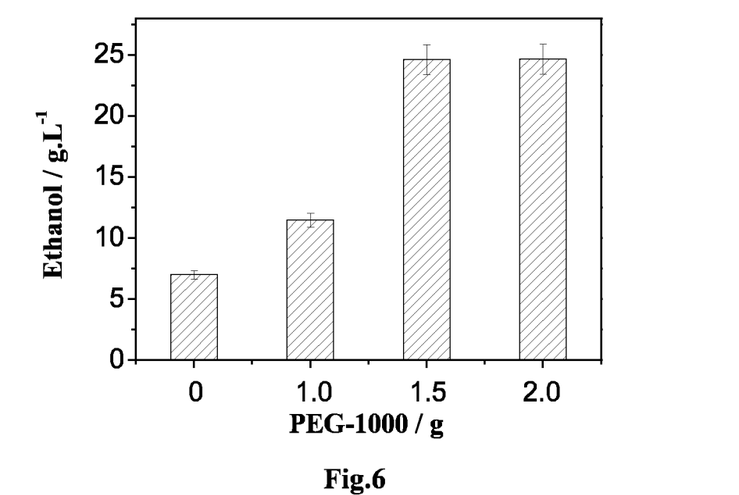
FIG. 6 illustrates effects of different concentrations of PEG-1000 on the ethanol concentration of non-detoxification steam exploded fast-growing poplar SSCF process.

The pretreated fast-growing poplar powder of 1.5 g is used as a substrate, and firstly adding 12.0 mL buffer solution, 0.3 mL cellulase, 0-2.0 g surfactant, wherein the buffer solution has a pH value of 4.86, incubating for 24 hours at a temperature of 50° C., and then lowering the temperature to 33° C., then adding *Saccharomyces cerevisiae*, wherein the cell density is maintained $0.8*10^8$/mL, SSCF fermentation for 72 hours. The enzymatic hydrolysis rate, ethanol yield and concentration data of the pretreated fast-growing poplar are shown in FIGS. 4, 5 and 6. It can be seen from the data in the Figs that PEG-1000 has little effect on the enzymolysis rate, while the ethanol yield and concentration increase with the increase of PEG-1000 concentration.

Example 27

The pretreated fast-growing poplar powder of 1.5 g is used as a substrate, and firstly adding 12.0 mL buffer solution, 0.3 mL cellulase, wherein the buffer solution has a pH value of 4.86, incubating for 4 hours at a temperature of 50° C., and then lowering the temperature to 33° C., then adding 1.5002 g surfactant of PEG-1000, wherein the cell density is maintained 0.8*108/mL, SSCF fermentation for 72 hours. The enzymatic hydrolysis rate, ethanol yield and concentration data of the pretreated fast-growing poplar are shown in table 5. It can be seen from the data in the table that the addition order of PEG-1000 has no significant effect on the enzymolysis rate, the ethanol yield and concentration, as compared with Example 10 and Example 12.

Example 28

The experimental procedure is the same as in Example 27 except that the added surfactant is 2.0039 g PEG-1000. The enzymatic hydrolysis rate and ethanol concentration data are shown in Table 5.

Example 29

The experimental procedure is the same as in Example 27 except that the pretreated fast-growing poplar is subjected to pre-enzymatic hydrolysis for 8 hours, the enzymatic hydrolysis rate, ethanol yield and concentration data are shown in Table 5.

Example 30

The experimental procedure is the same as in Example 30 except that the pretreated fast-growing poplar is subjected to pre-enzymatic hydrolysis for 8 hours, and the added surfactant is 2.0103 g PEG-1000. The enzymatic hydrolysis rate, ethanol yield and concentration data are shown in Table 5.

TABLE 5

Simultaneous saccharification and co-fermentation of pretreated fast-growing poplar

| Example | PEG-1000 | Time/h | Enzymatic hydrolysis rate/% | Ethanol yield/ % | Ethanol/ g/L |
|---|---|---|---|---|---|
| 27 | 1.5002 | 4 + 72 | 71.63 | 71.42 | 22.89 |
| 28 | 2.0039 | 4 + 72 | 71.82 | 70.90 | 22.17 |
| 29 | 1.5003 | 8 + 72 | 75.51 | 74.63 | 23.61 |
| 30 | 2.0103 | 8 + 72 | 74.93 | 73.84 | 24.01 |

We claim:

1. A surfactant-improved simultaneous saccharification and ethanol fermentation method for lignocellulose, wherein a pretreated lignocellulose substrate is directly subjected to the simultaneous saccharification and ethanol fermentation without any detoxification treatment by adding a surfactant with a concentration of 0.125 g~0.18 g/mL, wherein the surfactant is added after pre-enzymolysis, the method comprises:

mixing the pre-treated lignocellulose as a substrate, a cellulase, and a pH buffer solution to incubate and conduct the pre-enzymolysis for a period of time at a raised temperature for obtaining a resulting hydrolyzed mixture;

lowering the raised temperature; and adding the surfactant and *Saccharomyces cerevisiae* to the hydrolyzed mixture for the simultaneous saccharification and ethanol fermentation to produce ethanol.

2. The method, as recited in claim 1, wherein the surfactant is selected from the group consisting of polyethylene glycol (PEG), polyethylene glycol monomethyl Ether (MPEG), polyethylene glycol dimethyl ether (NHD), polydimethylsiloxane (PDMS), and combinations thereof.

3. The method, as recited in claim 1, wherein the surfactant is polyethylene glycol having a molecular weight of 200~8000.

4. The method, as recited in claim 1, wherein the amount of the substrate is 0.1-0.3 g/mL buffer; an loading of the cellulase is 10-30 FPU/g substrate; the cell density of the

*Saccharomyces cerevisiae* is $0.5*10^8$-$1.8*10^8$ cells/mL; the pre-enzymolysis temperature is 50° C. and the pre-enzymolysis is conducted for 2 to 24 hours; the temperature of the simultaneous saccharification and ethanol fermentation is 30 to 39° C.; the simultaneous saccharification and ethanol fermentation time is 16-96 hours.

5. The method, as recited in claim 1, wherein the pH buffer solution comprises at least one selected from the group consisting of acetic acid-sodium acetate, citric acid-sodium citrate, phosphoric acid-sodium phosphate buffer, and sulfuric acid solution, wherein the pH buffer solution has a pH value of 4.0~5.5.

6. The method, as recited in claim 1, wherein the amount of the substrate is 0.125 g/mL buffer.

7. The method, as recited in claim 1, wherein the loading of the cellulase is 30 FPU/g dry lignocellulose substrate.

8. The method, as recited in claim 1, wherein the cell density of *Saccharomyces cerevisiae* is $0.8*10^8$~$0.96*10^8$ cells/mL.

\* \* \* \* \*